US006549794B1

(12) United States Patent
Nadeau, Jr. et al.

(10) Patent No.: US 6,549,794 B1
(45) Date of Patent: Apr. 15, 2003

(54) SINGLE USE DISPOSABLE PROTECTIVE CAP

(75) Inventors: Richard G. Nadeau, Jr., Medford, NJ (US); Ernel O. Simpson, Yardley, PA (US)

(73) Assignee: Cytometrics, LLC, Exton, PA (US)

( * ) Notice: Subject to any disclaimer, the term of this patent is extended or adjusted under 35 U.S.C. 154(b) by 159 days.

(21) Appl. No.: 09/667,804

(22) Filed: Sep. 22, 2000

Related U.S. Application Data

(60) Provisional application No. 60/155,642, filed on Sep. 24, 1999, and provisional application No. 60/227,572, filed on Aug. 25, 2000.

(51) Int. Cl.$^7$ .................................................. A61B 5/00
(52) U.S. Cl. ........................ 600/310; 359/511; 600/121
(58) Field of Search ................................. 600/121, 122, 600/124, 175, 310–344; 422/58; 359/507, 511; 220/265

(56) References Cited

U.S. PATENT DOCUMENTS

| | | | |
|---|---|---|---|
| 3,809,072 A | 5/1974 | Ersek et al. ................... 128/23 |
| 3,929,018 A | 12/1975 | Turner ....................... 73/343 R |
| 4,183,248 A | 1/1980 | West ....................... 73/362 AR |
| 4,522,196 A | 6/1985 | Cunningham et al. .......... 128/4 |
| 4,646,722 A | 3/1987 | Silverstein et al. ............. 128/4 |
| 4,741,326 A | 5/1988 | Sidall et al. ................... 128/4 |
| 4,878,485 A | 11/1989 | Adair ........................... 128/6 |
| 5,088,834 A | 2/1992 | Howe et al. ................ 374/158 |
| 5,163,418 A | 11/1992 | Fraden et al. ................. 128/9 |
| 5,168,863 A | 12/1992 | Kurtzer ......................... 128/4 |
| 5,193,525 A | 3/1993 | Silverstein et al. ............. 128/4 |
| 5,201,908 A | 4/1993 | Jones ............................ 128/4 |
| 5,257,617 A | 11/1993 | Takahashi ..................... 128/4 |
| 5,318,029 A | 6/1994 | Palese ........................ 128/652 |
| 5,337,734 A | 8/1994 | Saab .............................. 128/4 |
| 5,400,791 A | 3/1995 | Schlier et al. ............... 128/664 |
| 5,443,781 A | 8/1995 | Saab ........................... 264/291 |
| 5,489,256 A | 2/1996 | Adair ......................... 600/133 |
| 5,516,010 A | 5/1996 | O'Hara et al. ............... 600/121 |
| 5,609,564 A | 3/1997 | Makita et al. ............... 600/200 |

(List continued on next page.)

FOREIGN PATENT DOCUMENTS

| | | | |
|---|---|---|---|
| EP | 0 135 134 A2 | 3/1985 | ............ A61B/5/02 |
| JP | 11-47098 | 2/1999 | ............ A61B/5/00 |
| WO | WO 93/14688 | 8/1993 | ............ A61B/1/00 |
| WO | WO 97/15229 | 5/1997 | ............ A61B/5/00 |
| WO | WO 97/25913 | 7/1997 | ............ A61B/5/00 |
| WO | WO 99/05961 | 2/1999 | ............ A61B/5/00 |
| WO | WO 99/16353 | 4/1999 | ............ A61B/5/05 |
| WO | WO 01/19235 A1 | 3/2001 | ............ A61B/1/04 |

OTHER PUBLICATIONS

Handbook of Optics vol. 11 Devices, Measurements, and Properties, $2^{nd}$ Edition (McGraw–Hill, NY, 1995).

*Primary Examiner*—Eric F. Winakur
*Assistant Examiner*—David McCrosky
(74) *Attorney, Agent, or Firm*—Caesar, Rivise, Bernstein, Cohen & Pokotilow, Ltd.

(57) ABSTRACT

A disposable protective cap and method for covering a probe in a spectral imaging apparatus are provided. The cap protects the probe from direct contact with a subject's tissues. The cap is hollow and elongated to cover the probe, having an open end and a closed end. At the closed end is an optically transparent face. This permits light to be transmitted from the probe through the closed end of the cap with minimal optical distortion. At the open end of the cap are components which interact with the probe to assure that the cap is not used more than one time. These components can use electrical interaction to assure only a single disposable use of the cap. Mechanically interacting components can also be used, either alone or in combination with electrically interacting components to assure only a single use of the cap.

8 Claims, 12 Drawing Sheets

U.S. PATENT DOCUMENTS

| | | | |
|---|---|---|---|
| 5,630,782 A | 5/1997 | Adair | 600/133 |
| 5,685,822 A | 11/1997 | Harhen | 600/125 |
| 5,695,447 A | 12/1997 | Yabe et al. | 600/121 |
| 5,695,449 A | 12/1997 | Moriyama | 600/122 |
| 5,704,892 A | 1/1998 | Adair | 600/121 |
| 5,707,343 A | 1/1998 | O'Hara et al. | 600/121 |
| 5,722,933 A * | 3/1998 | Yabe et al. | 600/121 |
| 5,792,049 A | 8/1998 | Eppstein et al. | 600/306 |
| 5,795,067 A | 8/1998 | Fraden et al. | 374/358 |
| 5,830,146 A | 11/1998 | Skladnev et al. | 600/478 |
| 5,840,014 A | 11/1998 | Miyano et al. | 60/125 |
| 5,924,977 A | 7/1999 | Yabe et al. | 600/121 |
| 5,974,338 A | 10/1999 | Asano et al. | 600/323 |

* cited by examiner

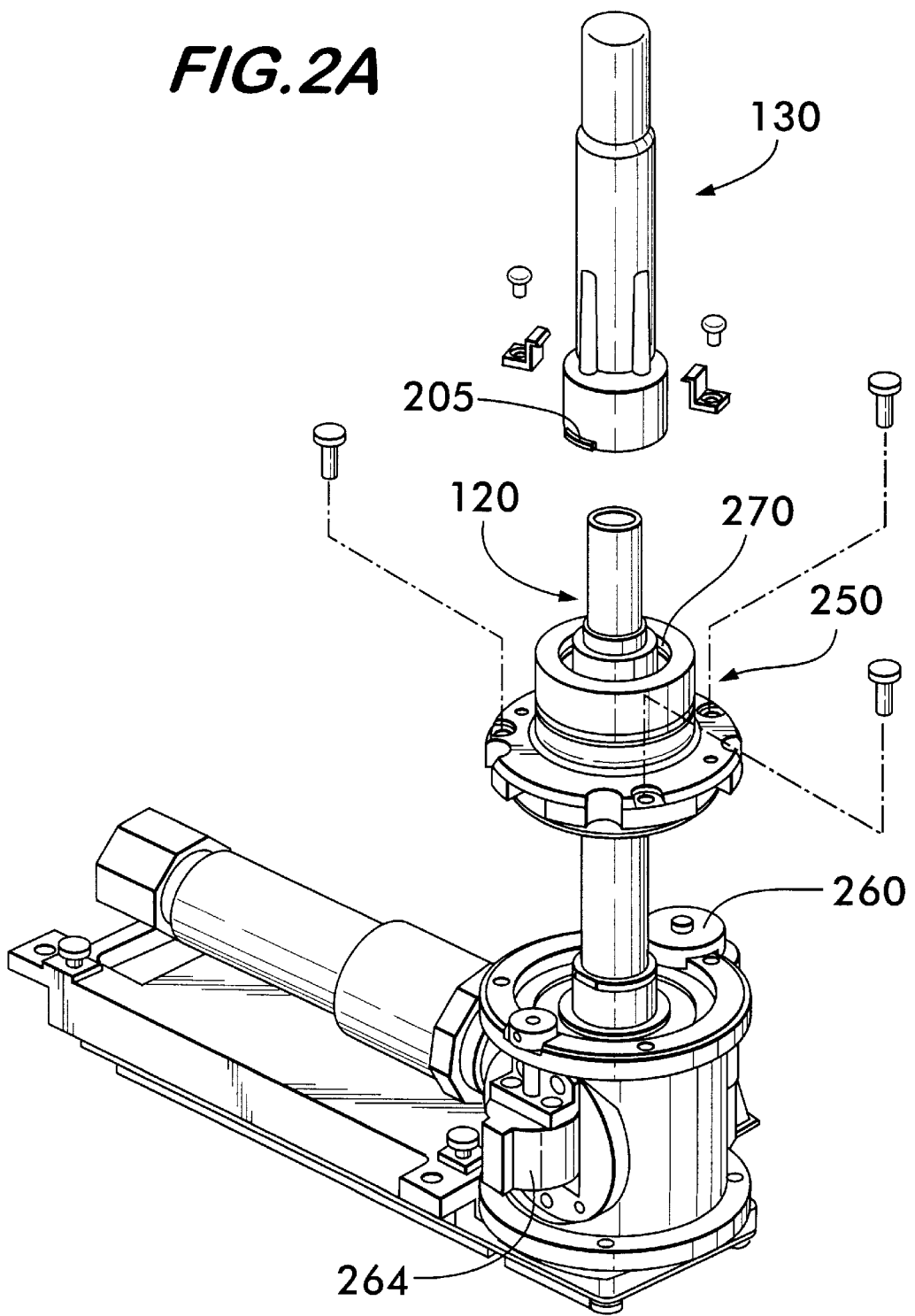

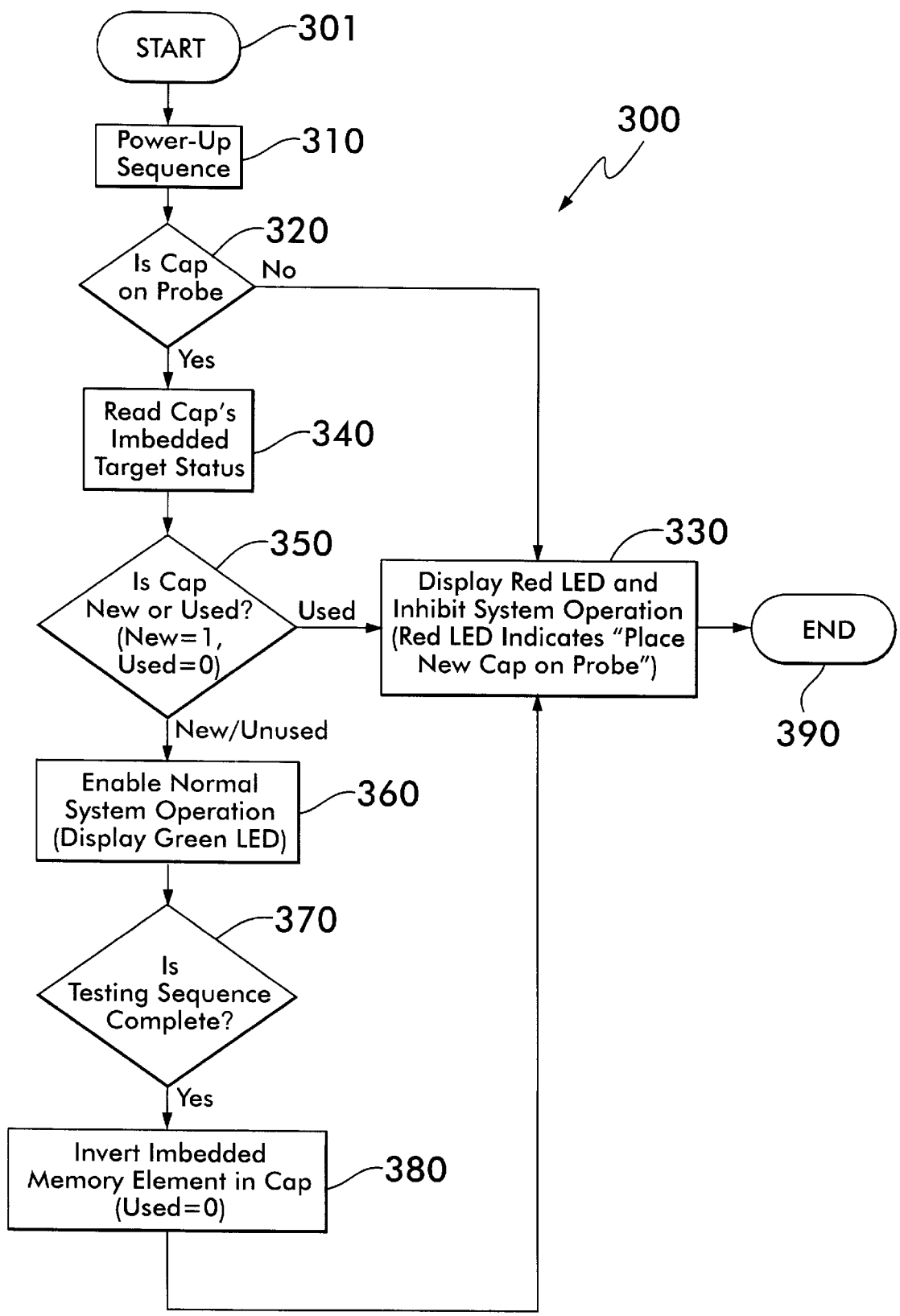

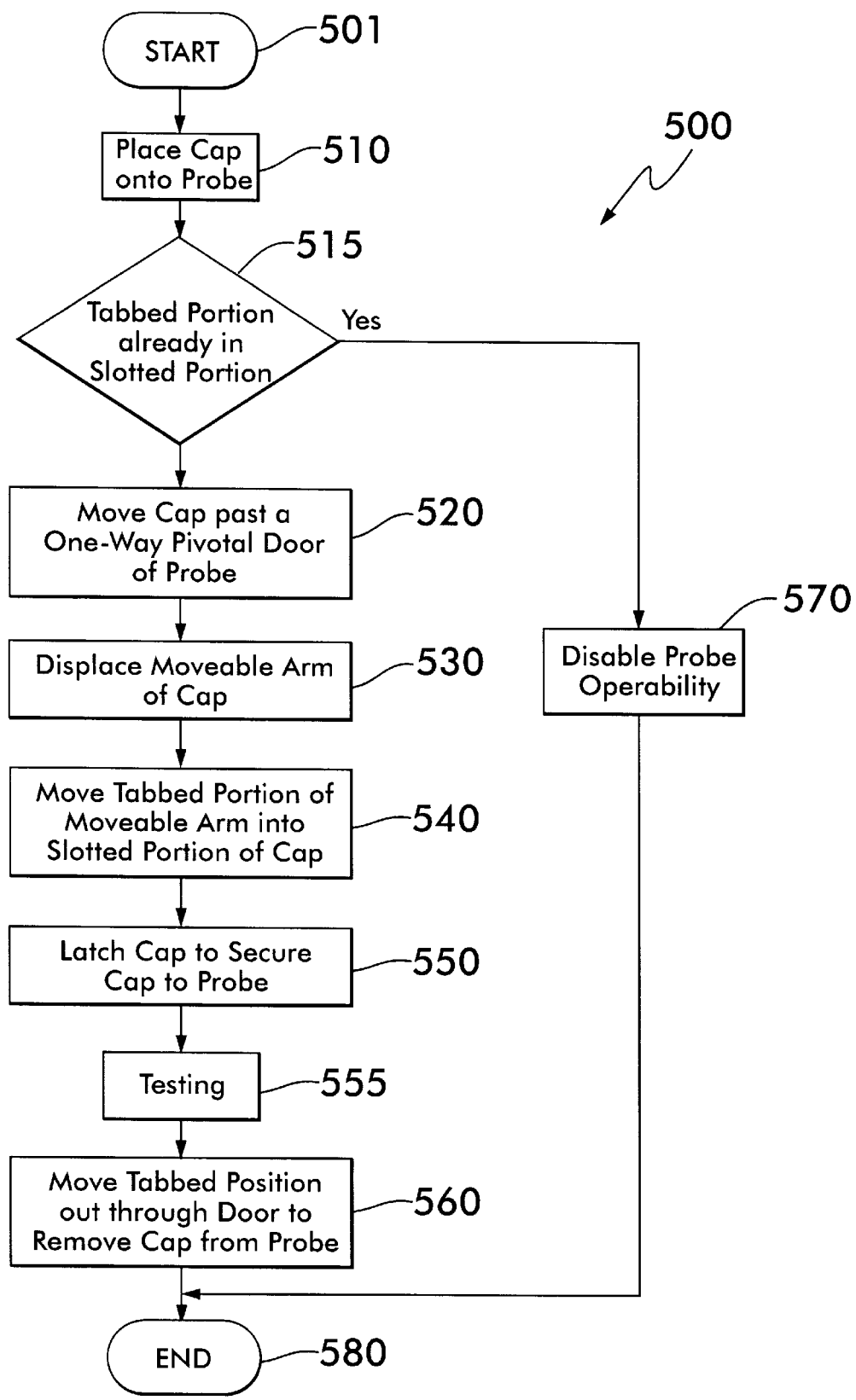

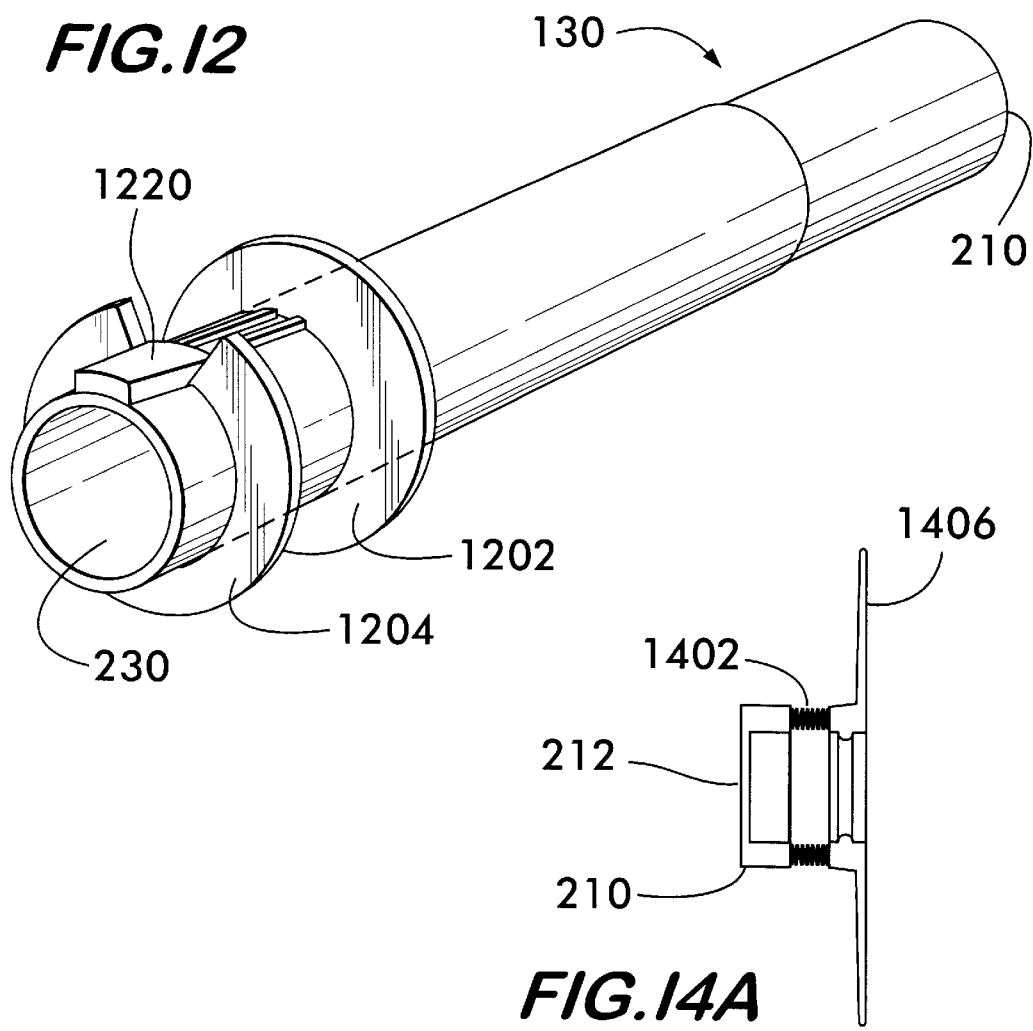
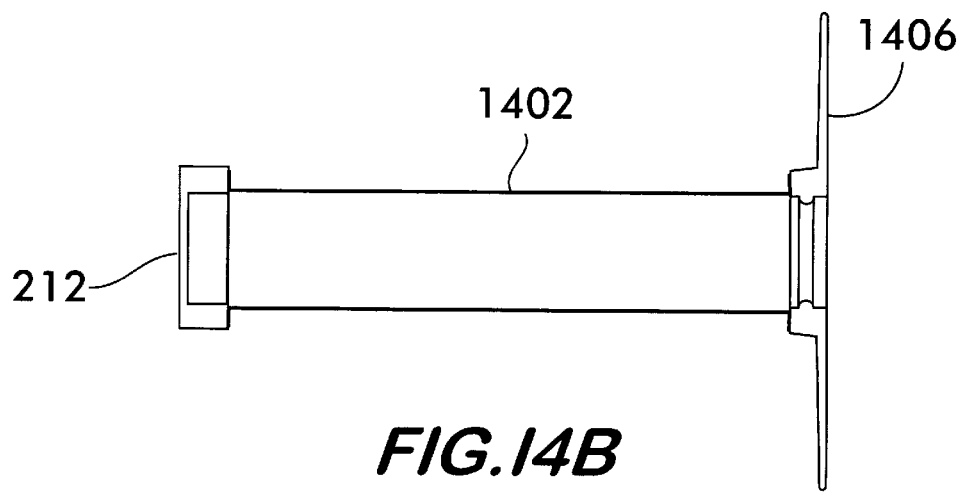

SINGLE USE DISPOSABLE PROTECTIVE CAP

CROSS-REFERENCE TO RELATED APPLICATION

The following United States utility patent applications have a common assignee and contain some common disclosure:

"Single Use Disposable Protective Cap," U.S. patent application Ser. No. 60/155,642, by Simpson et al., filed Sep. 24, 1999, which is incorporated by reference herein in its entirety. The present application claims priority of application Ser. No. 60/155,642 under 35 U.S.C. §119(e).

"Disposable Protective Covering for Medical Instruments," U.S. patent application Ser. No. 60/227,572, filed Aug. 25, 2000, which is incorporated by reference herein in its entirety (hereinafter referred to as "the '572 application"). The present application claims priority of the '572 application under 35 U.S.C. §119(e).

"Method and Apparatus for Providing High Contrast Imaging," U.S. patent application Ser. No. 09/401,859, by Christopher Cook and Mark M. Meyers, filed Sep. 22,1999, which is incorporated by reference herein in its entirety.

BACKGROUND OF THE INVENTION

1. Field of the Invention

This invention relates to disposable protective caps for use on medical instruments. More particularly, the invention relates to a disposable protective cap for use on spectral imaging devices.

2. Related Art

An important aspect of diagnosing health problems is the ability to analyze and test a subject's tissue and blood. Non-invasive analysis of a subject's tissue and blood is advantageous because it does not involve a high risk of injury caused by the testing procedure itself. For example, non-invasive analyses typically avoid puncturing body parts or changing bodily functions, e.g. blood flow, infection levels, vital signs, etc.

Typically, a spectral imaging apparatus is used for non-invasive analysis of a subject's tissue and blood. The spectral imaging apparatus has a probe with a polarized light source. The probe is used to project an illumination pattern within a region of interest and beneath a surface of the region of interest. A spectral imaging apparatus of this type can be used for measuring and testing. For example, hemoglobin levels can be measured using the spectral imaging apparatus to aid in diagnosing anemia and other diseases involving abnormal red blood cell count. The spectral imaging apparatus can also be used for analysis based solely upon imaging the region of interest. For example, the apparatus can be used to obtain images of tissues to be analyzed by an expert. The expert can use these images to determine the presence of cancerous cells within a particular region.

Using a spectral imaging apparatus to probe a variety of subjects requires the use of a probe cover. The cover, or probe cap, must not block or interfere with the illumination pattern which the probe projects. In order to avoid interference with the illumination pattern, the cap has a window at its end which transmits light. The window is said to have a low birefringence. Low birefringence of the window ensures that the optical properties of the probe will be substantially unaffected by the cap.

It is of critical importance that a cap be used. The same spectral imaging apparatus is typically used on a variety of subjects. The cap reduces the likelihood of spreading contagious diseases from one patient to the next. Without the cap, the probe could contact dangerous viruses and other infectious materials in one subject and transmit them to another subject. For that reason, it is important that the cap be made for disposable use. In addition, it is important that the same cap is not used on more than one subject in order to avoid contamination of the subject and degrade optical performance that can adversely affect the analysis. Beyond the risk of transmitting disease, inaccurate results based erroneously on a different subject's blood or tissues could dangerously lead to the wrong diagnosis.

Although a conventional probe cap can be made disposable, it is the user of the apparatus who must remember to actually dispose of the conventional cap after each use. During the course of a busy day of testing, even the most cautious user can make the mistake of forgetting to dispose of the probe cap. Even just one such error, on any given day, risks great harm to all subjects being tested with a used cap.

What is needed, therefore, is a disposable probe cover that is easy to install and remove and cannot be accidentally reused.

SUMMARY OF THE INVENTION

The present invention is a disposable protective cap for covering a probe for a spectral imaging apparatus. The cap protects the probe from direct contact with a subject's tissues. The cap is hollow and elongated to cover the probe, having an open end and a closed end. An optically transparent face is located at the closed end. This permits light to be transmitted from the probe through the closed end of the cap with minimal optical distortion. At the open end, the cap includes components which interact with the probe to assure that the cap is not used more than one time. In some embodiments, these components interact electrically to assure only a single disposable use of the cap. In other embodiments, this is accomplished through mechanical interaction. A combination of electrical and mechanical interaction is used in other embodiments to assure only a single use of the cap.

FEATURES AND ADVANTAGES OF THE INVENTION

The probe cap of the present invention advantageously avoids the serious health and contamination risks associated with using conventional probe caps. Instead of relying on a lack of human error as is done using conventional probe caps, this invention includes components on the cap to assure only a single disposable use. The present invention will not permit a spectral imaging apparatus to become operable with a used cap on the probe. The components on the probe cap of the present invention interact with the probe electrically, mechanically, or both to ensure that the probe only operates with a new cap.

BRIEF DESCRIPTION OF FIGURES

The accompanying drawings, which are incorporated herein and form part of the specification; illustrate the present invention and, together with the description, further serve to explain the principles of the invention and to enable a person skilled in the pertinent art to make and use the invention. In the drawings, like reference numbers indicate identical or functionally similar elements. Additionally, the leftmost digit(s) of a reference number identifies the drawing in which the reference number first appears.

FIG. 2A shows a focusing assembly according to an embodiment of the present invention;

FIG. 3 is a flowchart of a method to assure only a single use of the cap of FIG. 2;

FIG. 5 is a flowchart of a method of assuring only a single use of the cap of FIGS. 4A through 4C;

FIG. 12 illustrates an embodiment including two rings to assure only a single use of the cap;

FIGS. 14A and 14B illustrate a collapsed and expanded view respectively of an embodiment including a stretchable body of the cap.

DETAILED DESCRIPTION OF THE PREFERRED EMBODIMENTS

Figure 1:
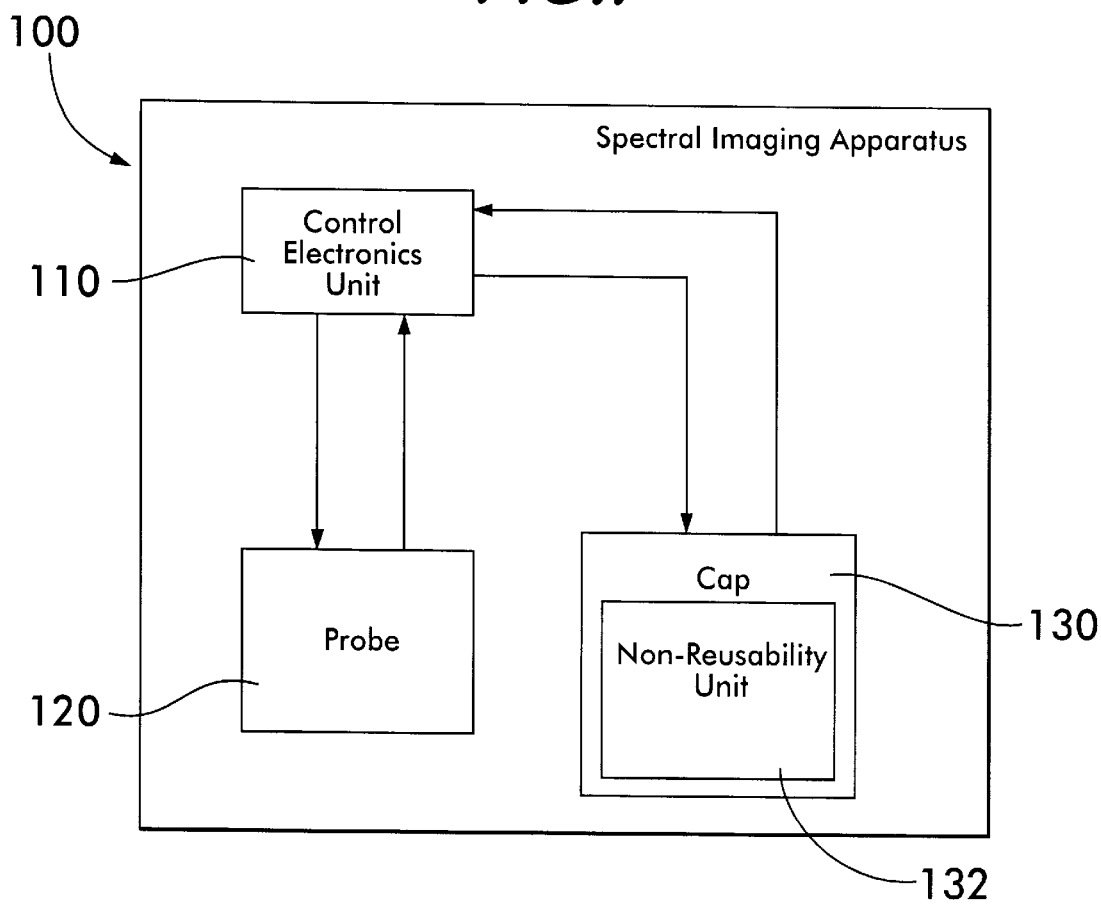
FIG. 1 shows a high level block diagram of a spectral imaging apparatus according to an embodiment of the present invention.

FIG. 1 illustrates a high level block diagram of a spectral imaging apparatus 100. Spectral imaging apparatus 100 includes a control electronics unit 110, a probe 120 and a cap 130. Spectral imaging apparatus 100 is preferably, but not necessarily, of the type described in commonly assigned U.S. Pat. No. 5,983,120, issued Nov. 9, 1999, in the names of Warren Groner and Richard G. Nadeau, and entitled "Method and Apparatus for Reflected Imaging Analysis" (hereinafter referred to as "the '120 patent"), or in commonly assigned U.S. Pat. No. 6,104,939, issued Aug. 15, 2000, in the names of Warren Groner and Richard G. Nadeau, and entitled "Method and Apparatus for Reflected Imaging Analysis" (hereinafter referred to as "the '939 patent"). The disclosures of the '120 patent and the '939 patent are incorporated herein by reference as though set forth in their entireties.

According to the present invention, cap 130 includes a non-reusability unit 132 located at an open end portion of cap 130. Non-reusability unit 132 cooperates with probe 120 to permit cap 130 to be operatively mounted to probe 120 only once. Control electronics unit 110 can be any commercially available microprocessor and associated peripheral circuitry. Control electronics unit 110 can also be any suitable application specific integrated circuit (ASIC) for controlling the operation of spectral imaging apparatus 100.

Control electronics unit 110 can be mounted to probe 120. Control electronics unit 110 can also be mounted at a suitable location elsewhere within spectral imaging apparatus 100. Non-reusability unit 132 can electronically communicate status information regarding cap 130 to control electronics unit 110. This information can be used to disable operability of probe 120 if it is determined that cap 130 has already been used. Non-reusability unit 132 can also mechanically cooperate with probe 120 to prevent cap 130 from being operatively mounted more than once. It will be apparent to those skilled in the relevant arts that spectral imaging apparatus 100 contains many other components, including a housing, a light source for illuminating a region of interest, etc. These elements are not shown for convenience of description of the inventive features.

Figure 2:
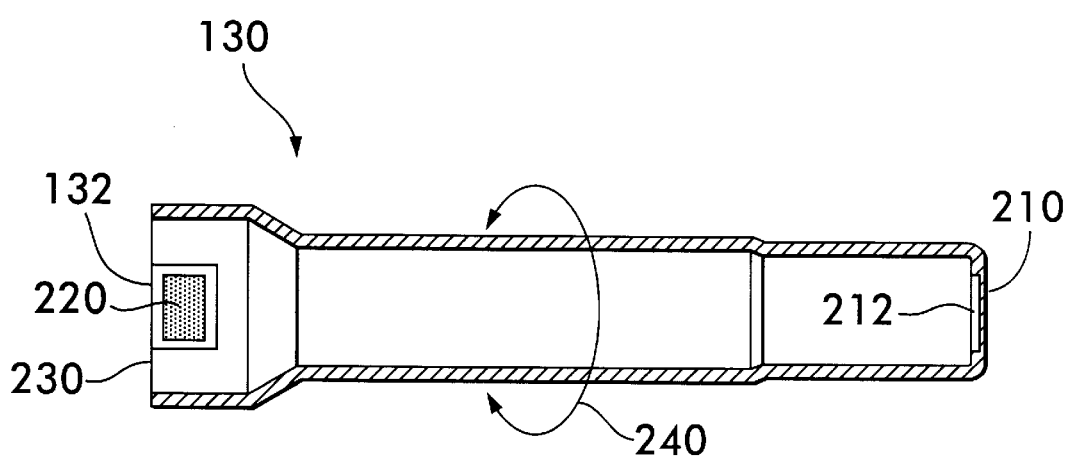
FIG. 2 shows an embodiment including magnetic material to assure only a single use of the cap.

FIG. 2 shows an embodiment of the present invention wherein non-reusability unit 132 includes magnetic material 220. Also shown in FIG. 2 are closed end portion 210 of cap 130, open end portion 230 of cap 130 and probe body 240. Closed end portion 210 includes an optically transparent face portion 212 which permits light to be transmitted with minimal optical distortion. In a preferred embodiment, optical distortion is abated by adjusting the following properties for optically transparent face portion 212: transmittance, flatness, polarization distortion, and glare. Transmittance is measured as a ratio of the light intensity measured by spectral imaging apparatus 100 with cap 130 installed thereon to the light intensity measured by spectral imaging apparatus 100 without cap 130. Transmittance through optically transparent face portion 212 should be equal to or greater than ninety percent from 500 nanometers (nm) to 650 nm.

Optical flatness for optically transparent face portion 212 should be equal to or less than six fringes, as measured interferometrically, at 635 nm. For example, if the diameter of cap 130 is approximately five millimeters (mm), the optical flatness should be less than two microns in surface variation across the five mm diameter, assuming the optical flatness is measured interferometrically by reflection across the surface.

Polarization distortion is considered by measuring a change in degree of polarization (DOP), a change in degree of linear polarization (DOLP) and a change in degree of circular polarization (DOCP), due to cap 130. These three parameters identify any degradation of linear polarization purity on passage of polarized light through cap 130. At 635 nm in a preferred embodiment, neither DOP nor DOLP should exceed two percent, and DOCP should not exceed six percent.

The glare parameters are based on a cap glare count and cap glare ratio. To determine cap glare count, one must measure the "light-on dark levels." The light-on dark levels are detector light intensity levels when probe 120, with a light source on, is placed in a dark container or room. The light-on dark level is measured with cap 130 installed and designated as $I_{ldc}$. The light-on dark level is also measured without cap 130 and designated as $I_{ld}$. The difference between $I_{ldc}$ and $I_{ld}$ represents the cap glare count. Preferably, the cap glare count should not exceed seventy five. Ideally both $I_{ldc}$ and $I_{ld}$ should be equivalent to $I_d$, which represents the detector dark or zero level when the light source is off for probe 120. However, due to internal light reflections and light scatter inside probe 120, in the case of $I_{ld}$, and due to additional light reflections and scatter from cap 130, in the case of $I_{ldc}$, these intensity levels are always greater than the detector zero level.

The cap glare ratio is a measured ratio of additional light glare due to the presence of cap 130 over the light glare due to probe 120, or $[I_{ldc}-I_{ld}]/[I_{ld}-I_d]$. Preferably, the cap glare ratio should not exceed five.

In an embodiment, cap 130, including both closed end portion 210 and open end portion 230, can be formed in one piece from clear plastic. Materials, such as acrylics, polycarbonate, clear polyesters, clear ABS, clear PVC, Cyclic-Olefin polymers or other clear plastic material, can be used for this purpose. A clear plastic material with a low birefringence having a light transmission of at least 90% between 350 nm and 750 nm can be used.

In another embodiment, cap 130 can be formed in two pieces. In this embodiment, probe body 240 is formed from plastic material or a rubber modified polymer. However, optically transparent face portion 212 is made from a clear plastic material. In an embodiment, optically transparent face portion 212 is an anti-reflective coated glass.

Cap 130 can also include a protective shield (not shown) that protects spectral imaging apparatus 100 from body fluids or other contaminants. In one embodiment of the present invention, the protective shield (not shown) can be a separate piece of plastic that is joined to cap 130. In another embodiment, the protective shield can be the same piece of plastic used to form cap 130. The protective shield is preferably, but not necessarily, of the type described as a protective covering (e.g., shield or drape) in the '572 application.

FIG. 2A illustrates an exploded view of a focusing assembly for the present invention. More specifically, FIG. 2A shows the relationship of a focusing mechanism 250 to cap 130 and probe 120, according to an embodiment of the present invention. As shown, focusing mechanism 250 fits over the objective lens of probe 120 and attaches to a base containing a stepper motor 260 and an encoder 264. As described above, cap 130 fits over probe 120 to become operatively mounted. Located at the base of cap 130 is one or more securing mechanisms 205 for attaching cap 130 to spectral imaging apparatus 100. Securing mechanisms 205 can be a catch for a latch, a Luer lock that fits a threaded region, or the like. Securing mechanisms 205 (shown in FIG. 2A as securing mechanism 205) attaches to a securing region 270. Securing region 270 (e.g., latch, thread, and the like) aligns cap 130 such that optically transparent face portion 212 is concentric to the objective window (not shown) of probe 120. Securing region 270 is the part of focusing mechanism 250 that is used to move either cap 130 or probe 120 towards or away from the subject. The entire focusing assembly (namely, focusing mechanism 250, stepper motor 260, encoder 264) are housed within spectral imaging apparatus 100.

In a preferred embodiment, focusing mechanism 250 is configured to traverse cap 130 with respect to probe 120. Holding probe 120 in a fixed position, focusing mechanism 250 moves cap 130 inward and outward to adjust the focus of optical images captured by spectral imaging apparatus 100. Focusing mechanism 250 uses stepper motor 260 and encoder 264 in a closed loop controller system to position cap 130 to any depth in a specified range. As described, focusing mechanism 250 is integrated with securing mechanism 205 that holds cap 130. In operation, stepper motor 260 turns a spur gear that translates securing mechanism 205 along the optical axis of probe 120, via a lead screw mechanism. Simultaneously, the spur gear turns the shaft of encoder 264 allowing precise location of cap 130. In an embodiment, focusing mechanism 250 moves in step sizes of less than or equal to three microns.

Focusing mechanism 250 also functions to minimize the birefringence angle. The negative range of motion is the distance traveled inward. The negative range of motion should be sufficient to guarantee that the closed end portion 210 of cap 130 touches probe 120. Focusing mechanism 250 has the capability to report the position of cap 130 with respect to probe 120. Therefore, an operator of spectral imaging apparatus 100 can measure the distance between the closed end portion 210 and probe 120, as well as instruct spectral imaging apparatus 100 to locate cap 130 to a specified distance.

As discussed in reference to FIG. 2, in an embodiment, non-reusability unit 132 includes magnetic material 220. Magnetic material 220 is typically composed of materials such as ferrite, metglass, or other materials which exhibit magnetostrictive properties. In an embodiment, magnetic material 220 is located at open end portion 230 out of the optical path of light transmitted by probe 120. Magnetic material 220 can be imbedded within the material used to fabricate cap 130. Magnetic material 220 can also be secured to the surface of cap 130. Magnetic material 220 is capable of being sensitized or desensitized. This provides a transduction capability so that the sensitized or desensitized state of magnetic material 220 represents cap status as being either used or unused. Signals indicating the state of magnetic material 220 are sent to spectral imaging apparatus 100. Spectral imaging apparatus 100 can include a sensor (not shown) to detect the magnetic polarity of magnetic material 220. Magnetic sensors, such as a coil, differential amplifier and other circuitry could be employed for this purpose. The magnetic polarity is communicated to control electronics unit 110. Control electronics unit 110 typically processes this information using system software. Control electronics unit 110 determines whether the cap status is used or unused. If the cap status is determined to be unused, then probe 120 is enabled. If the cap status is determined to be used, then probe 120 is disabled. In that instance, probe 120 can no longer be used to take measurements. Spectral imaging apparatus 100 can display or otherwise indicate cap status to the user of spectral imaging apparatus 100.

FIG. 3 illustrates a general operational flow of an embodiment of the present invention. More specifically, flowchart 300 shows an example of the general operational flow for the embodiment of FIG. 2 to assure only a single use of cap 130. FIG. 3 begins at step 301 and passes immediately to step 310. At step 310, spectral imaging apparatus 100 is powered up. A power up sequence is accomplished using system software and control electronics unit 110. Conventional methods of initializing processing systems, also referred to as boot methods, can be employed for this purpose.

At step 320, spectral imaging apparatus 100 determines whether cap 130 has been placed on probe 120. This determination is made either through remote or mechanical detection. If it is determined that no cap is present on probe 120, then probe operability is disabled at step 330.

At step 340, the probe sensor (not shown) senses the polarity of magnetic material 220. System software processes this information to determine if cap 130 is used or unused at step 350. If it is determined that cap 130 is used, then control passes to step 330, where probe operability is disabled. If it is determined that cap 130 is unused, then probe operability is enabled at step 360.

At step 370, a periodic determination is made as to whether the current sequence of probe measurements is complete. If it is determined that the current probe measurement sequence is complete, then at step 380, cap status is set to "used." The probe sensor (not shown) transmits an electromagnetic pulse to magnetic material 220. This desensitizes magnetic material 220. Probe operability is disabled at step 330 and remains disabled until an unused cap is placed onto the probe. The control flow of flowchart 300 then ends as indicated by step 390.

Figure 4A:
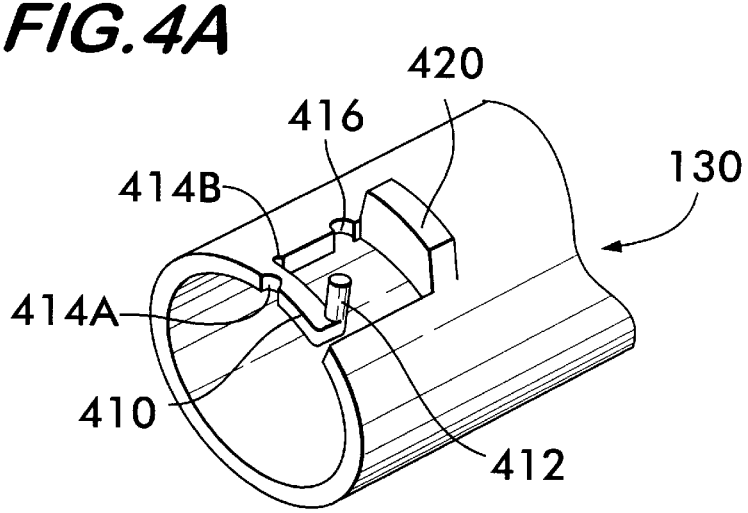
FIGS. 4A, 4B and 4C illustrate multiple views of an embodiment in which the cap cooperates mechanically with the probe to assure only a single use of the cap.
Figure 4B:
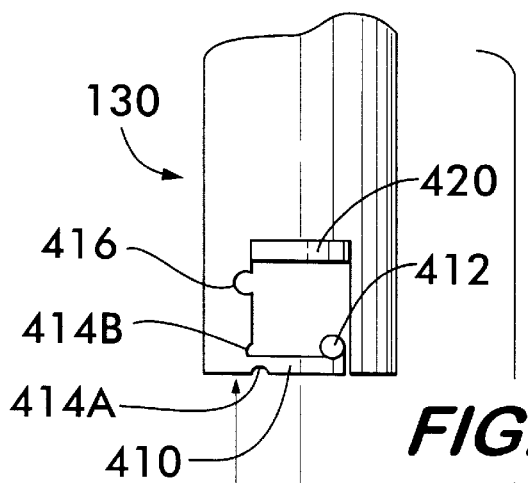
Figure 4C:
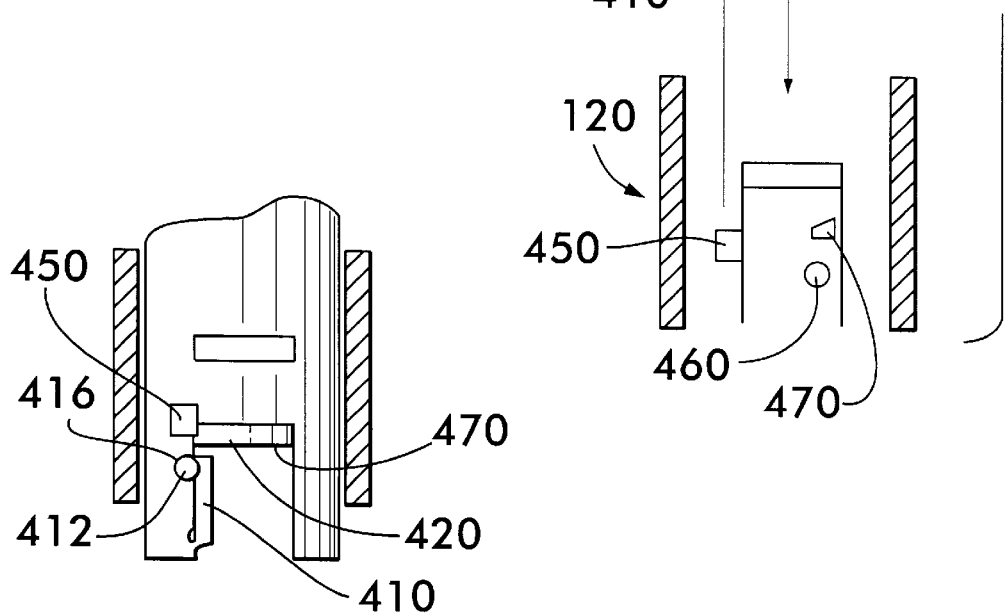

FIGS. 4A through 4C illustrate another embodiment of the present invention in which non-reusability unit 132 cooperates mechanically with probe 120 to prevent cap 130 from being operatively mounted more than once. FIG. 4A shows a three dimensional view of cap 130 according to this embodiment. Cap 130 includes a movable arm 410, a slotted portion 416, and a latch catch 420. Movable arm 410 has a tabbed portion 412. Movable arm 410 can also have at least one notched portion 414A and 414B. FIGS. 4B and 4C are top views illustrating how non-reusability unit 132 cooperates mechanically with probe 120. FIG. 4B shows non-reusability unit 132 in relation to probe 120 prior to cap 130 being latched into position. Probe 120 as adapted to be used for this embodiment has a one-way pivotal door 450, an impact pin 460, and a latch 470 for securing cap 130 to probe 120. As cap 130 is pushed onto probe 120, impact pin 460 displaces movable arm 410 and forces tabbed portion 412 to snap into slotted portion 416. Impact pin 460 protrudes from the surface of probe 120. Impact pin 460 can be shaped to prevent shearing of arm 410 upon impact. For example, pin 460 could be rounded or otherwise suitably shaped for this purpose. Portions 414A and 414B act as hinges to ease angular movement of arm 410. Tabbed portion 412 protrudes outward from the surface of cap 130. Tabbed portion 412 can be round or otherwise shaped. Tabbed portion 412 must be shaped to fit the shape of slotted portion 416.

FIG. 4C shows tabbed portion 412 after it has snapped into place in slotted portion 416. This occurs behind one-way pivotal door 450. One-way pivotal door 450 allows cap 130 to be removed because door 450 only swings one way. Once cap 130 is removed, it cannot be reused because tabbed portion 412 (if snapped into slotted portion 416) would be restricted from passing through door 450. Moreover, since tabbed portion 412 would be inhibited from passing through door 450, tabbed portion 412 would likewise restrict latch 470 from grabbing catch 420. Additionally, arm 410 is molded at an angle so that it bends in only one direction. Removal of tabbed portion 412 from slotted portion 416 would break arm 410. Accordingly, cap 130 is designed and structured to be prevented from being operatively mounted on probe 120 more than once.

FIG. 5 illustrates a general operational flow of an embodiment of the present invention. More specifically, flowchart 500 shows an example of the general operational flow for the embodiment shown in FIGS. 4A through 4C. More particularly, flowchart 500 is a method of assuring only one operable mounting of cap 130 as embodied in FIGS. 4A through 4C. FIG. 5 begins at step 501 and passes immediately to step 510. At step 510, cap 130 is placed onto probe 120. At step 515, if tabbed portion 412 is already fixed in slotted portion 416 then control passes to step 570, where probe operability is disabled. At step 520, cap 130 is moved past a one-way pivotal door 450 of probe 120. At step 530, movable arm 410 is angularly displaced. At step 540, tabbed portion 412 is moved into slotted portion 416. This results in the combination of tabbed portion 412 in slotted portion 416 being aligned with one-way pivotal door 450. At step 550, cap 130 is latched to secure it to probe 120. Probe 120 is used for a testing or measuring sequence at step 555. After testing or measuring is complete, at step 560, cap 130 is unlatched. Tabbed portion 412, still in slotted portion 416, is moved back out through one-way pivotal door 450 to remove cap 130 from probe 120. The control flow of flowchart 500 then ends as indicated by step 580.

Figure 6A:
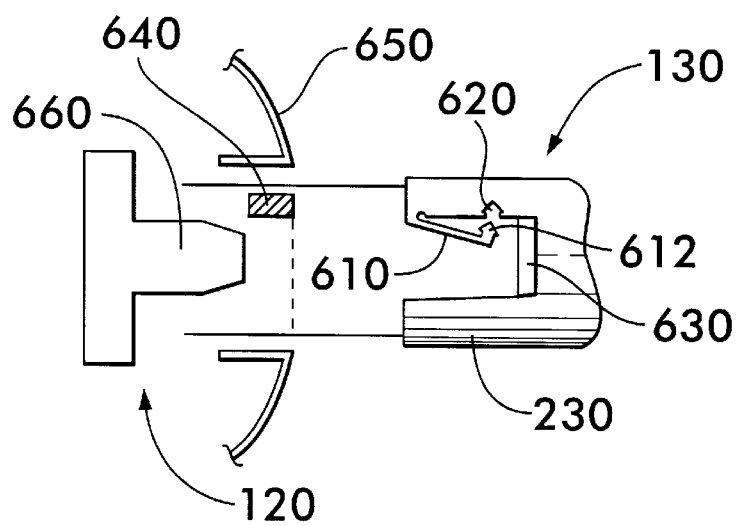
FIGS. 6A, 6B and 6C illustrate multiple views of an embodiment in which the cap cooperates mechanically and electrically with the probe to assure only a single use of the cap.
Figure 6B:
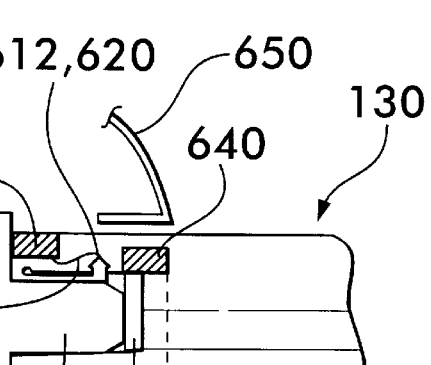
Figure 6C:
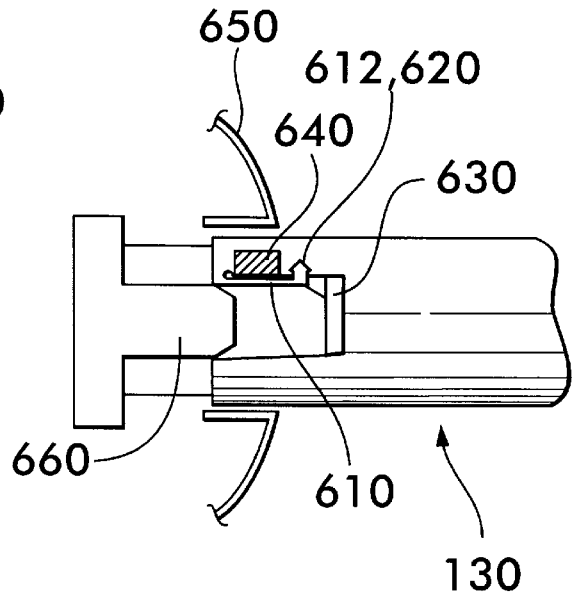

FIGS. 6A through 6C illustrate top views of an embodiment of the present invention in which non-reusability unit 132 cooperates mechanically and electrically with probe 120 to prevent cap 130 from being operatively mounted more than once. FIG. 6A shows open end 230 of cap 130 including a latch catch 630, a movable arm 610, a tabbed portion 612 of movable arm 610, and a slotted portion 620 shaped to permit tabbed portion 612 to become fixed therein. For example, tabbed portion can be triangularly wedge-shaped and slotted portion 620 can also be triangularly shaped. Other suitably paired shapes for tabbed portion 612 and slotted portion 620 could be used. Door 640, arm 610, tabbed portion 612, and slotted portion 620 can be located either on the left or right side of open end 230. FIG. 6A also shows probe 120 adapted to interact with this embodiment. Included in probe 120 and housing 650 are a displacement wedge 660 and a one-way pivotal door 640.

FIG. 6B shows cap 130 after it has been operatively mounted to probe 120 and latched to catch 630. Catch 630 protrudes from the outer surface of cap 130. FIG. 6B shows a switch 670 on probe 120 and a wire 680 on cap 130. Wire 680 connects switch 670 to slotted portion 620. Wire 680 can be any suitable conductive channel. Switch 670 is positioned so that it does not interfere with the optical measuring characteristics of probe 120. As cap 130 is initially moved toward displacement wedge 660, the movement of tabbed portion 612 is not inhibited by door 640.

As shown in FIG. 6A, movable arm 610 is initially at a sufficient angle so that tabbed portion 612 is not aligned with door 640. After tabbed portion 612 is moved beyond door 640, arm 610 contacts displacement wedge 660. This causes arm 610 to be angularly displaced until tabbed portion 612 becomes fixed in slotted portion 620. When tabbed portion 612 is fixed in slotted portion 620, tabbed portion 612 contacts wire 680. This trips switch 670 to signal control electronics unit 110 that a new cap 130 has been placed on probe 120. As a result, operability of probe 120 is enabled.

FIG. 6C shows cap 130 after it has been partially ejected from probe 120. Tabbed portion 612 remains fixed in slotted portion 620 as cap 130 moves from the position shown in FIG. 6B to the position shown in FIG. 6C. During ejection of cap 130, tabbed portion 612 impacts one-way pivotal door 640. This causes door 640 to pivot outwardly to permit cap 130 to obtain the position shown in FIG. 6C. The same cap 130, with tabbed portion 612 fixed in slotted portion 620 will be prevented from being operatively mounted again. If cap 130 were pushed back onto probe 120, then tabbed portion 612 would impact one-way pivotal door 640. Door 640 will not pivot inwardly. In that case, door 640 would prevent cap 130 from being operatively mounted. Additionally, arm 610 is molded at an angle so that it bends in only one direction. Removal of tabbed portion 612 from slotted portion 620 would break arm 610. If arm 610 is broken off or if tabbed portion 612 were broken off from arm 610, then cap 130 could move beyond door 640 and be latched to catch 630. However, without tabbed portion 612, switch 670 could not be tripped. Control electronics unit 110 could not be signaled to enable operability of probe 120 without tabbed portion 612.

Figure 7:
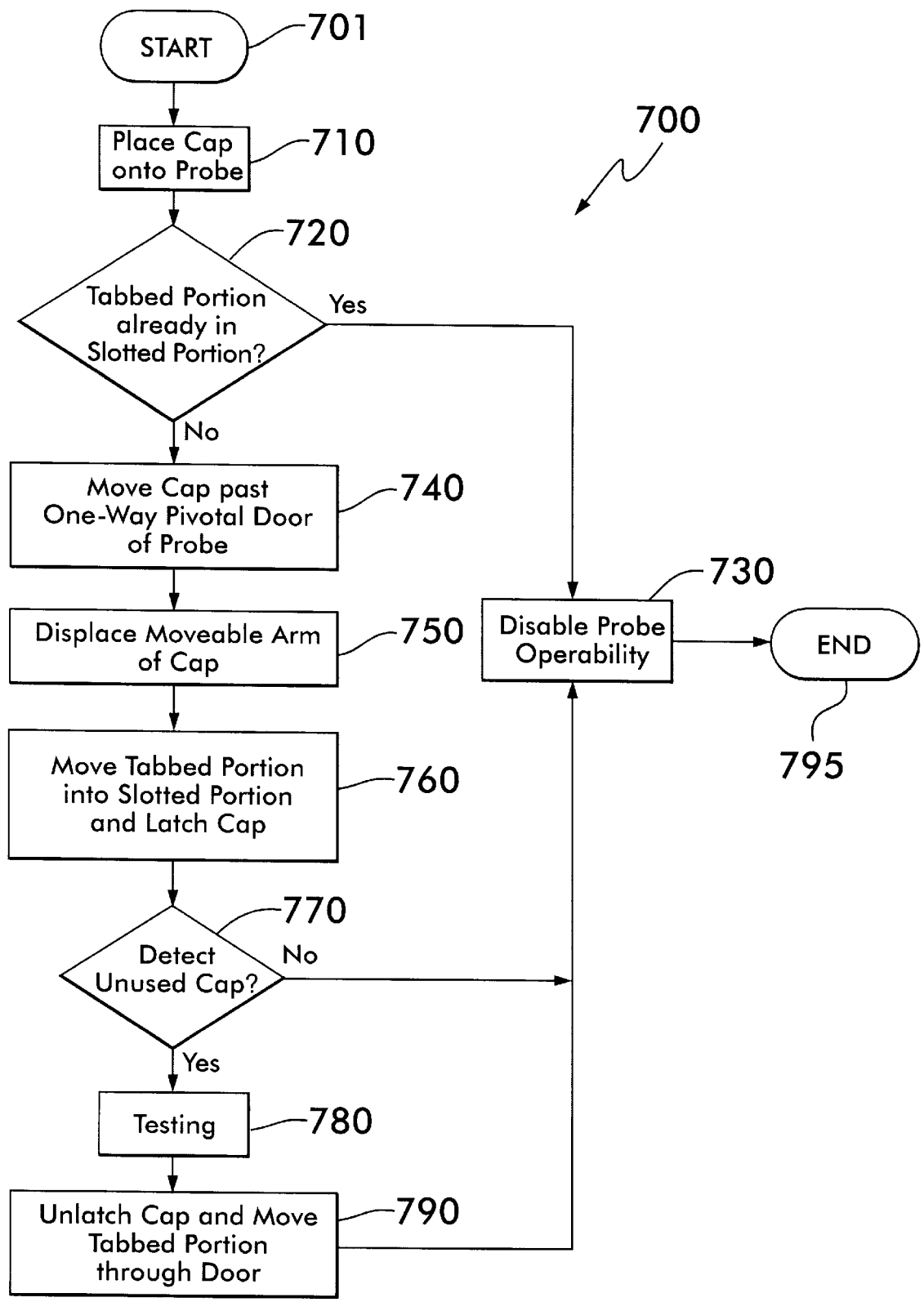
FIG. 7 is a flowchart of a method to assure only a single use of the cap of FIG. 6.

FIG. 7 illustrates a general operational flow of an embodiment of the present invention. More specifically, flowchart 700 shows an example of the general operational flow for the embodiment shown in FIGS. 6A–6C. More particularly, flowchart 700 is a method of assuring only one operable mounting of cap 130 as embodied in FIGS. 6A–6C.

FIG. 7 begins at step 701 and passes immediately to step 710. At step 710, cap 130 is placed on probe 120. Operability of probe 120 has not yet been enabled. At step 720, if tabbed portion 612 is already in slotted portion 620, then cap 130 cannot be operatively mounted. Tabbed portion 612 will impact one-way pivotal door 640. In that instance, control passes to step 730, where probe 120 remains in a disabled state and the user can place another cap 130 onto probe 120 at step 710. If tabbed portion 612 is not already in slotted portion 620, then door 640 is moved past tabbed portion 612 at step 740. At step 750, displacement wedge 660 impacts movable arm 610 after tabbed portion 612 has already cleared door 640. This occurs unless movable arm 610 has previously been broken off. At step 760, assuming an unbroken arm 610, tabbed portion 612 is moved into slotted portion 620. Latch catch 630 is latched and cap 130 is secured to probe 120. When tabbed portion 612 is fixed in slotted portion 620, tabbed portion 612 contacts wire 680. This trips switch 670 to signal control electronics unit 110 that an unused cap 130 is on probe 120, at step 770. Probe 120 is used for a testing or measuring sequence at step 780. After testing or measuring is complete, at step 790, cap 130 is unlatched removed. This is accomplished by tabbed portion 612 impacting door 640. Since door 640 pivots outwardly, cap 130 can be removed. If an unused cap is not detected at step 770, then control passes to step 730 and probe 120 is disabled. The control flow of flowchart 700 then ends as indicated by step 795.

Figure 8:
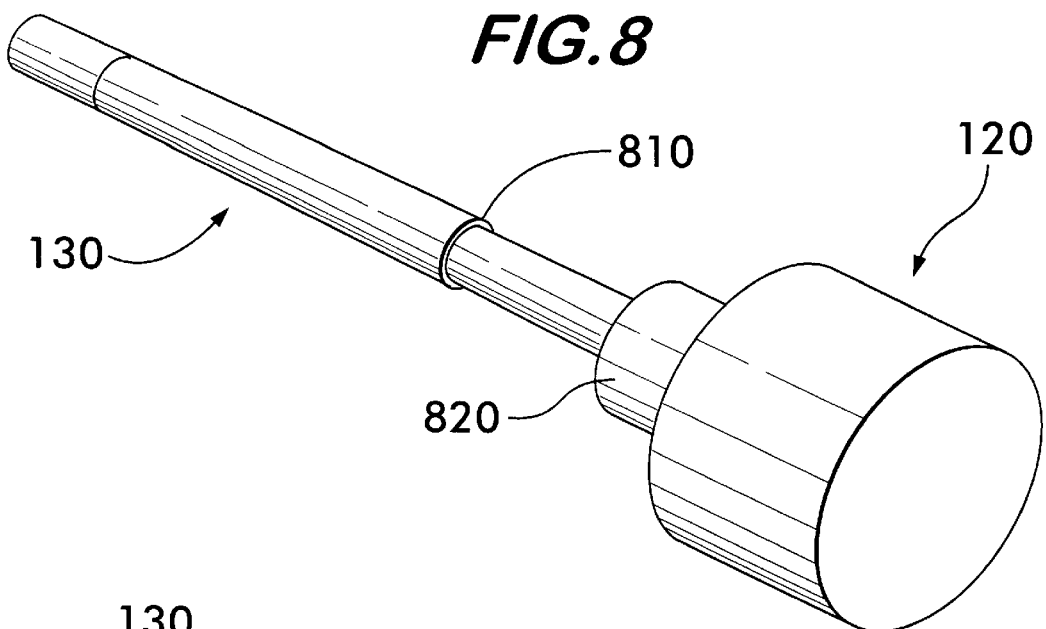
FIG. 8 illustrates an embodiment including conductive ink to assure only a single use of the cap.

FIG. 8 illustrates an embodiment of the present invention in which non-reusability unit 132 includes conductive ink 810 and probe 120 includes a coil 820. When open end portion 230 of cap 130 is moved through coil 820, a sensor (not shown) in spectral imaging apparatus 100 detects a change in inductance. The change in inductance is signaled to control electronics unit 110 to indicate that a new cap 130 has been placed on probe 120. Alternatively, a change in capacitance could also be detected. Control electronics unit 110 sends a pulse to coil 820 to induce a current in conductive ink 810. This current is of sufficient magnitude to heat conductive ink 810 until it open-circuits. Control electronics unit 110 will disable operability of probe 120 if cap 130 is mounted with ink 810 in the open circuited state.

Figure 9:
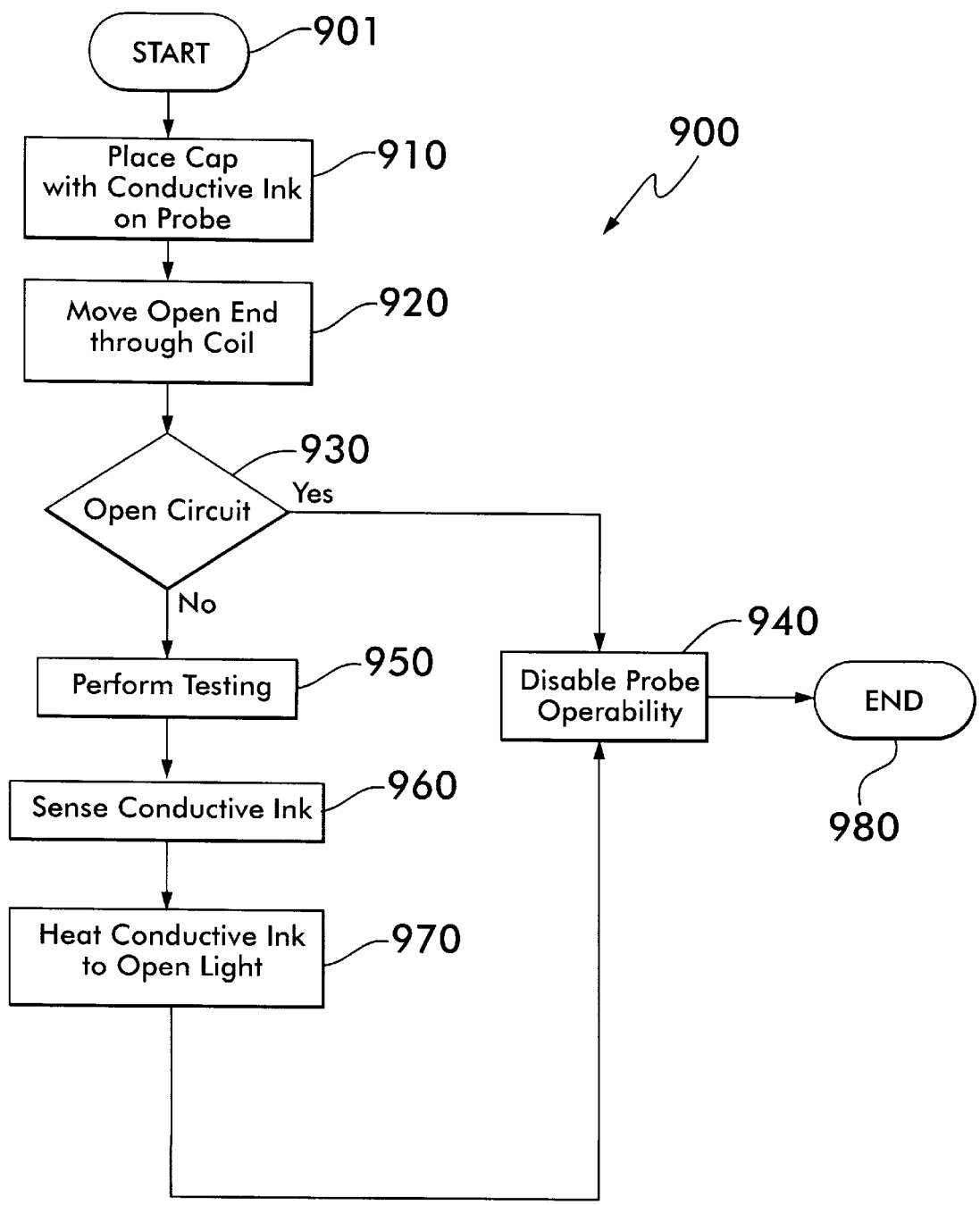
FIG. 9 is a flowchart of a method to assure only a single use of the cap of FIG. 8.

FIG. 9 illustrates a general operational flow of an embodiment of the present invention. More specifically, flowchart 900 shows an example of the general operational flow for the embodiment shown in FIG. 8. More particularly, flowchart 900 is a method of assuring only one operable mounting of cap 130 as embodied in FIG. 8.

FIG. 9 begins at step 901 and passes immediately to step 910. At step 910, cap 130 with conductive ink 810 is placed on probe 120. At step 920, open end portion 230 of cap 130 is moved through coil 820. At step 930, it is determined whether conductive ink 810 has already been open-circuited. If conductive ink 810 has already been open-circuited, then probe operability is disabled at step 940. In that case, control electronics unit 110 will not allow any measurements to be taken using spectral imaging apparatus 100. If conductive ink 810 has not been open-circuited, then control passes to step 950 where probe 120 is used to perform measuring or testing. After measuring or testing, conductive ink is sensed, at step 960, and conductive ink 810 is heated until it open-circuits, at step 970. Probe operability is disabled at step 940 and spectral imaging apparatus 100 cannot be used for measuring or testing if cap 130, with open-circuited conductive ink, is mounted on probe 120. The control flow of flowchart 900 then ends as indicated by step 980.

Figure 10A:
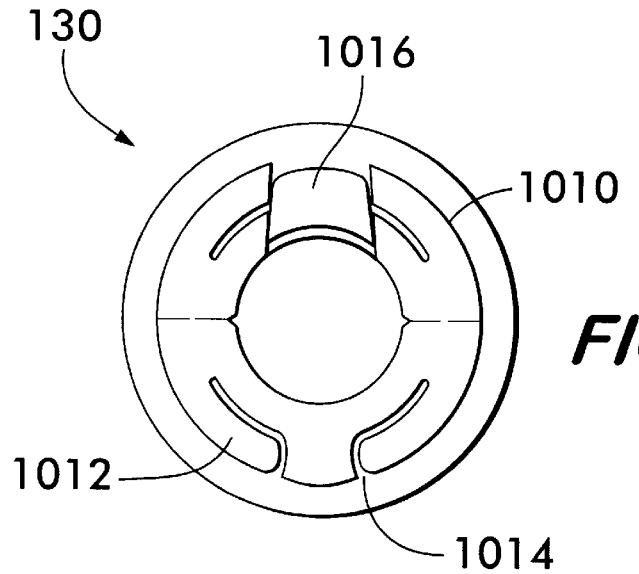
FIGS. 10A and 10B illustrate end and side views respectively of an embodiment including flarable portions to assure only a single use of the cap.
Figure 10B:
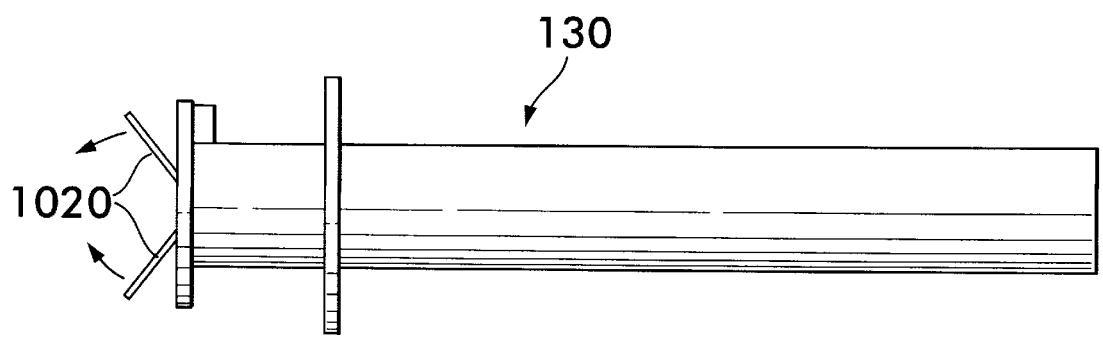

FIGS. 10A and 10B illustrate an embodiment of the present invention including a flarable ring 1010 with flarable end portions 1012 cut therefrom and a plurality of spring tabs 1020. Spring tabs 1020 fit through cuts 1014 and extend outwardly from cap 130. When cap 130 is mounted on probe 120 and latched securely into place, end portions 1012 are flared outwardly and cuts 1014 are spread by spring tabs 1020 which frees latch up 1016 to move to its molded position. Spring tabs 1020 fall downward after cap 130 is unlatched and ejected from probe 120. However, latch up 1016 would remain in its freed position and prevent cap 130 from being re-inserted onto probe 120. In this way, cap 130 is destructively changed and cannot be reused.

Figure 11A:
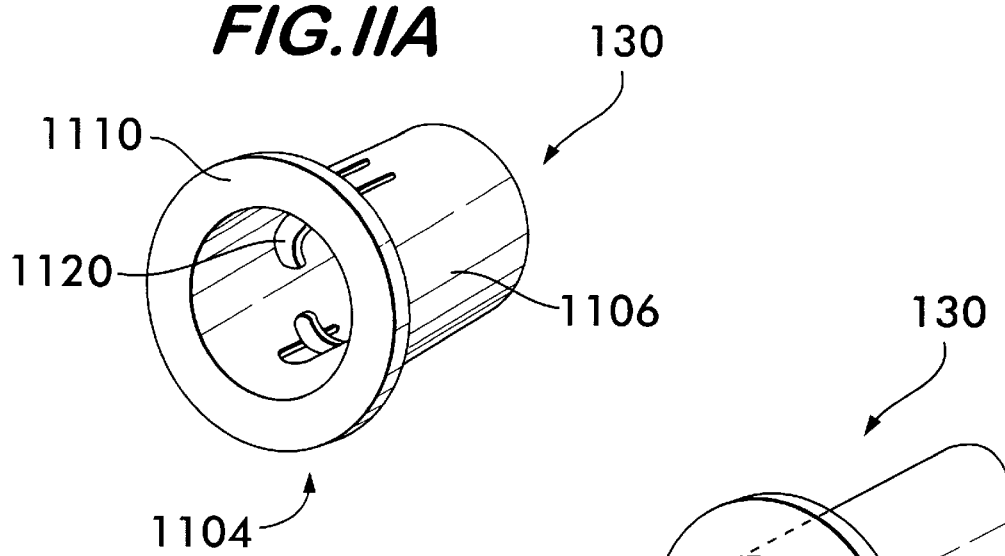
FIGS. 11A, 11B and 11C illustrate an embodiment including finger portions to assure only a single use of the cap.
Figure 11B:
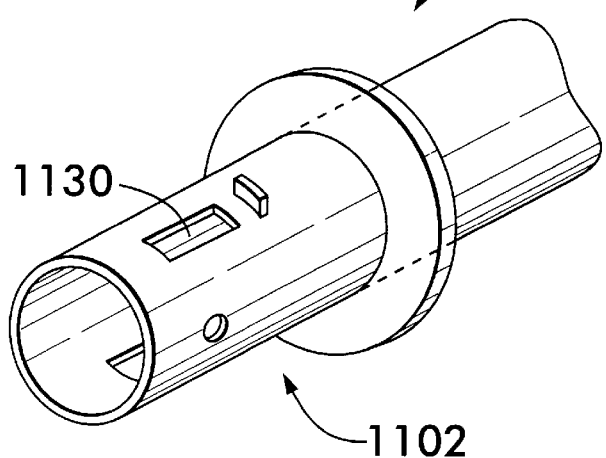
Figure 11C:
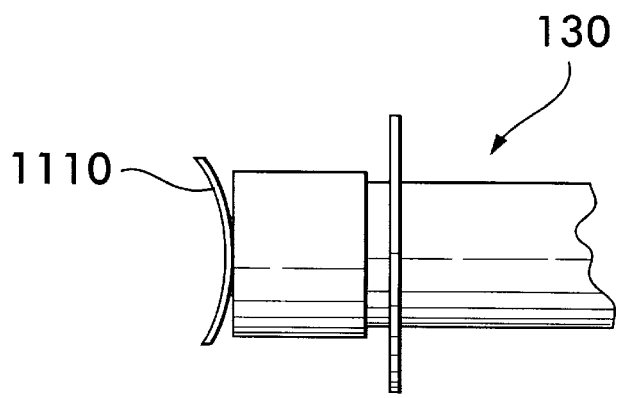

FIGS. 11A, 11B and 11C illustrate an embodiment of the present invention where cap 130 is constructed from a first part 1102 and a second part 1104. First part 1102 has a plurality of elongated slots 1130. Second part 1104 has a flexible concave ring 1110 at the edge of cap 130 and a tubular portion 1106 which is slidable over first part 1102. Tubular portion 1106 includes a plurality of flexible finger portions 1120 cut therefrom. Finger portions 1120 are fittable through elongated slots 1130 to secure first part 1102 to second part 1104. When cap 130 is mounted and latched to probe 120, finger portions 1120 are displaced by probe 120. When cap 130 is ejected from probe 120, finger portions 1120 remain in a position which blocks cap 130 from being remounted onto probe 120.

FIG. 12 illustrates an embodiment of the present invention where two rings are located at open end portion 230 of cap 130. A guard ring 1202 is permanently secured to cap 130. A break-away ring 1204 is connected to cap 130 by small runners (not shown) that will break when break-away ring 1204 comes into contact with minimum force. When cap 130 is mounted onto probe 120, break-away ring 1204 disconnects from the surface of cap 130, and a switch (not shown) is triggered on probe 120 to inform control electronics unit 110 that a new cap is present. A catch 1220 protrudes from the outer surface of open end portion 230 and enables cap 130 to be secured to probe 120 or spectral imaging apparatus 100.

Prior to being disconnected from the runners (not shown), break-away ring 1204 partially encircles cap 130 to form a c-shape. Catch 1220 is located so as to prevent break-away ring 1204 from completely encircling cap 130. As shown in FIG. 12, catch 1220 is positioned near open end portion 230 and extends towards closed end portion 210. In an preferred embodiment, the width of catch 1220 closest to open end portion 230 is smaller than the width of catch 1220 at the distal end from open end portion 230. When break-away ring 1204 is disconnected, break-away ring 1204 slides towards guard ring 1202. Once break-away ring 1204 clears catch 1220, break-away ring 1204 retracts to its molded position to completely or more closely encircle cap 130, such that break-away ring 1204 is prevented from being able to slide pass catch 1220. Thus, catch 1220 keeps break-away ring 1204 from being dislodged from cap 130. An advantage of this feature is that it eliminates the number of miscellaneous parts in an operating room or similar medical environment. However, it would be apparent to one skilled in the relevant art(s) that other structural modifications can be made to cap 130 to prevent break-away ring 1204 from being removed from cap 130.

After catch 1220 secures cap 130 onto probe 120, contact is made with guard ring 1202 to trigger a second switch (not shown) to inform control electronics unit 110 to enable probe 120 for operation. In an embodiment, spectral imaging apparatus 100 also includes an optical sensor (not shown) that scans the surface of cap 130. When the optical sensor (not shown) detects that break-away ring 1204 has made contact with guard ring 1202, the optical sensor (not shown)

would either activate the second switch (not shown) or inform control electronics unit 110 to enable probe 120 for operation.

In another embodiment, the optical sensor (not shown) scans the surface of cap 130 as cap 130 is secured onto probe 120. In this embodiment, once catch 1220 is secured to probe 120 or spectral imaging apparatus 100, a marked region (not shown) of cap 130 would be aligned with the optical sensor (not shown). The optical sensor (not shown) would read the marked region (not shown) and inform control electronics unit 110 to enable probe 120 for operation.

In yet another embodiment, the second switch (not shown) can be located at the latch or region (not shown) where catch 1220 is secured to probe 120 or spectral imaging apparatus 100. Thus, the second switch (not shown) can be activated when catch 1220 touches and is secured onto probe 120 or spectral imaging apparatus 100.

In all the above embodiments described in reference to FIG. 12, control electronics unit 110 can disable probe 120 from operation if cap 130 subsequently becomes unsecured during the operation. As such, in an embodiment, the second switch (not shown) or optical scanner (not shown) would continuously send signals to control electronics unit 110 as long as cap 130 is securely mounted. Moreover, cap 130 cannot be remounted if break-away ring 1204 is detached and, consequently, the first switch (not shown) cannot be activated.

Figure 13:
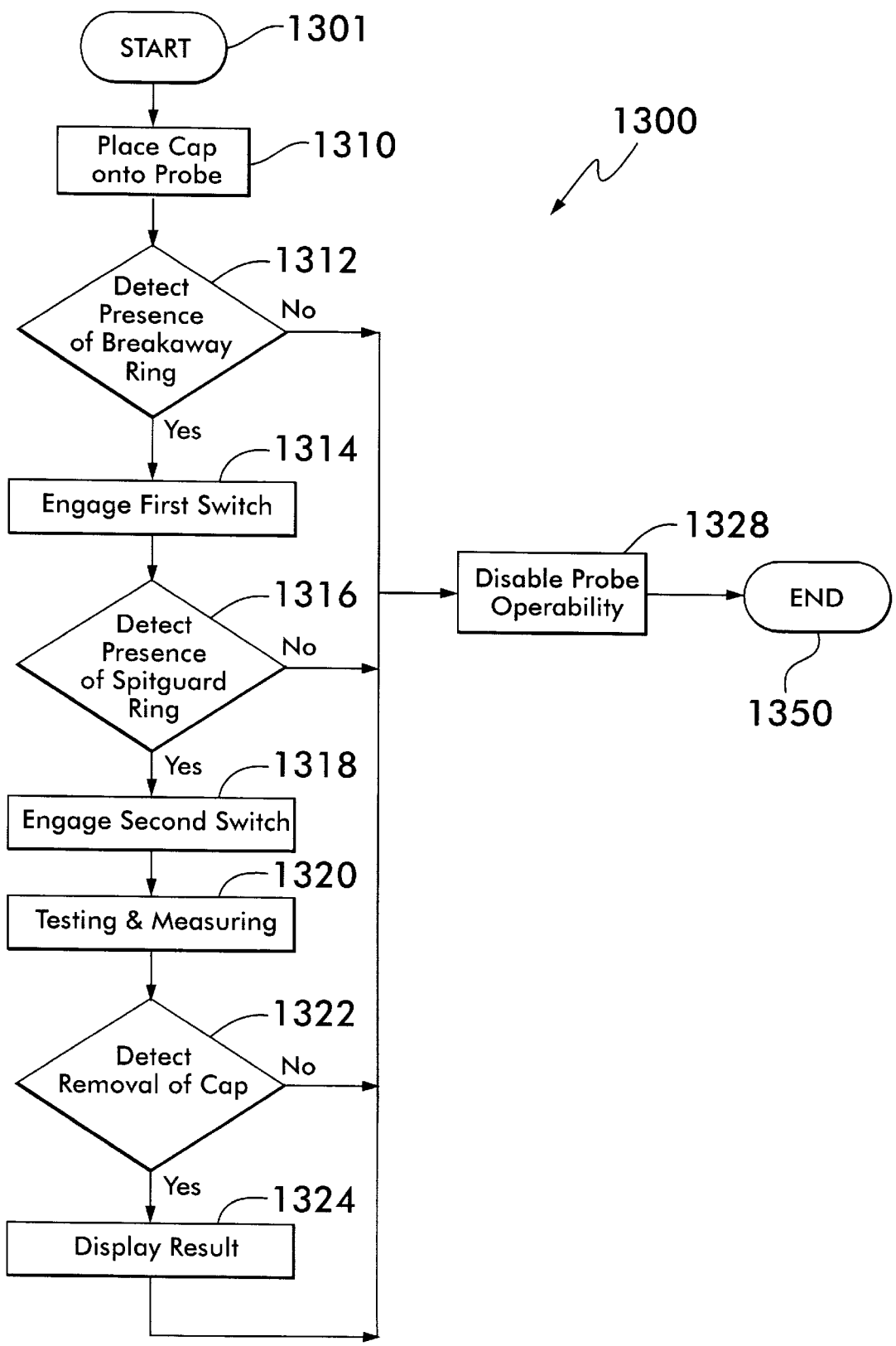
FIG. 13 is a flowchart of a method to assure only a single use of the cap of FIG. 12.

FIG. 13 illustrates a general operational flow of an embodiment of the present invention. More specifically, flowchart 1300 shows an example of the general operational flow for the embodiment shown in FIG. 12. More particularly, flowchart 1300 is a method of assuring only one operable mounting of cap 130 as embodied in FIG. 12.

FIG. 13 begins at step 1301 and passes immediately to step 1310. At step 1310, cap 130 is placed onto probe 120. At step 1312, control electronics unit 110 detects the presence of break-away ring 1204. As discussed in reference to FIG. 12, break-away ring 1204 disconnects from cap 130 when probe 120 makes contact with break-away ring 1204. When this occurs, at step 1314, a first switch (not shown) is activated on probe 120. If break-away ring 1204 is not present, control flow 1300 passes immediately to step 1328 and the first switch (not shown) is not activated. In this instance, at step 1328, control electronics unit 110 prevents the operability of probe 120, and control flow 1300 ends at step 1350.

If break-away ring 1204 is detected at step 1312 and the first switch (not shown) is activated at step 1314, control electronics unit 110 detects the presence of guard ring 1202 at step 1316. As discussed in reference to FIG. 12, guard ring 1202 is detected when probe 120 makes contact with guard ring 1202. When this occurs, at step 1318, a second switch (not shown) is activated on probe 120 to inform control electronics unit 110. If guard ring 1202 is not detected, control flow 1300 passes immediately to step 1328.

If guard ring 1202 is detected and the second switch (not shown) is activated, probe 120 is used for measurement or testing at step 1320. After measurement or testing is completed, cap 130 must be removed from probe 120. At step 1322, control electronics unit 110 detects the presence of cap 130. If cap 130 has not been removed, control flow 1300 passes to step 1328 where probe 120 is disabled from further operations. If cap 130 has been removed, the measurement or testing results are displayed at step 1324. Afterwards control flow 1300 passes to step 1328 to disable probe 120. Control flow 1300 then ends as indicated by step 1350.

FIGS. 14A and 14B illustrate an embodiment of the present invention where cap 130 is composed of a stretchable film or silicon-based material. Closed end portion 210 and open end portion 230 of cap 130 can be made of the same stretchable material or other clear plastic materials as discussed in reference to FIG. 2. FIG. 14B shows one view of cap 130 where cap 130 is stretched to cover probe 120. FIG. 14A shows another view of cap 130 before it is expanded to its full length.

The present invention (i.e., spectral imaging apparatus 100, control electronics unit 110, non-reusability unit 132, probe 120, or any part thereof) may be implemented using hardware, software or a combination thereof and may be implemented in one or more computer systems or other processing systems. Such implementations would be apparent to persons skilled in the relevant arts.

While various embodiments of the present invention have been described above, it should be understood that they have been presented by way of example, and not limitation. It will be apparent to persons skilled in the relevant art(s) that various changes in form and detail can be made therein without departing from the spirit and scope of the invention. Thus, the present invention should not be limited by any of the above described exemplary embodiments.

What is claimed is:

1. A disposable protective cap for covering a probe for use with a spectral imaging apparatus, comprising:

an elongated hollow member having an open end portion and a closed end portion,
wherein said member is removably disposable over at least one end portion of the probe to protect the probe from direct contact with an object during operation of the probe,
wherein said closed end portion includes an optically transparent face portion to permit light to be transmitted therethrough with minimal optical distortion,
wherein, during operation of the probe, an illumination pattern may be projected through said optically transparent face portion for illuminating the object within a region of interest; and
multiple use prevention means disposed at said open end portion and cooperating with the probe for permitting the cap to be operatively mounted to the probe only once.

2. The disposable protective cap of claim 1, wherein said cap comprises a surface and wherein said multiple use prevention means comprises:

a break-away ring encircling the cap, said break-away ring capable of disconnecting from the surface of the cap as the cap is mounted onto the probe to thereby activate a first switch located on the probe to send a first signal to a control unit within the spectral imaging apparatus to indicate the presence of an unused cap, wherein said control unit enables operability of the probe upon receipt of said first signal.

3. The disposable protective cap of claim 2, wherein said multiple use prevention means further comprises:

a guard ring located parallel to said break-away ring, said break-away ring being capable of sliding towards said guard ring.

4. The disposable protective cap of claim 3, wherein said guard ring is positioned to activate a second switch located on the probe if the cap is securely mounted onto the probe to send a second signal to said control unit if the cap is securely mounted, wherein said control unit enables operability of the probe upon receipt of said first signal and said second signal.

5. The disposable protective cap of claim 4, wherein said guard ring is positioned to activate said second switch to continuously send said second signal as long as the cap is securely mounted, wherein said control unit disables operability of the probe if said second switch ceases sending said second signal.

6. The disposable protective cap of claim 2, wherein the spectral imaging apparatus includes an optical scanner operational to scan the surface of the cap and continuously send a second signal to said control unit as long as the cap is securely mounted onto the probe, wherein said control unit enables operability of the probe upon receipt of said first signal and said second signal, and disables operability of the probe if said optical scanner ceases sending said second signal.

7. The disposable protective cap of claim 1, further comprising:
 a securing mechanism disposed at said open end portion, wherein said securing mechanism is removably attachable to the spectral imaging apparatus.

8. The disposable protective cap of claim 7, wherein said securing mechanism is removably attachable to a focusing mechanism of the spectral imaging apparatus, said focusing mechanism operable to move the cap relative to the probe.

* * * * *